United States Patent [19]

Terwilliger

[11] Patent Number: 4,911,173

[45] Date of Patent: Mar. 27, 1990

[54] BIOPSY ATTACHMENT FOR ULTRASOUND PROBE

[75] Inventor: Richard A. Terwilliger, San Ramon, Calif.

[73] Assignee: Diasonics, Inc., San Francisco, Calif.

[21] Appl. No.: 120,358

[22] Filed: Nov. 13, 1987

[51] Int. Cl.$^4$ ............................................. A61B 8/12
[52] U.S. Cl. ..................................... 128/662.06; 128/4
[58] Field of Search .................... 128/660, 661, 663, 4, 128/24 A

[56] References Cited

U.S. PATENT DOCUMENTS

| | | | |
|---|---|---|---|
| 4,058,114 | 11/1977 | Soldner | 128/660 |
| 4,346,717 | 8/1982 | Haerten | 128/660 |
| 4,402,324 | 9/1983 | Lindgren et al. | 128/660 |
| 4,548,210 | 10/1985 | Enjoji et al. | 128/660 |
| 4,567,896 | 2/1986 | Barnea et al. | 128/660 |
| 4,576,175 | 3/1986 | Epstein | 128/660 |
| 4,587,972 | 5/1986 | Morantee, Jr. | 128/4 |
| 4,608,989 | 9/1986 | Drue | 128/660 |
| 4,671,292 | 6/1987 | Matzuk | 128/660 |
| 4,681,103 | 7/1987 | Boner et al. | 128/660 |
| 4,742,829 | 5/1988 | Law et al. | 128/662.06 |
| 4,756,313 | 7/1988 | Terwilliger | 128/662.06 X |
| 4,763,662 | 8/1988 | Yokoi | 128/4 X |
| 4,817,616 | 4/1989 | Goldstein | 128/662.06 |

Primary Examiner—Francis Jaworski
Attorney, Agent, or Firm—Blakely, Sokoloff, Taylor & Zafman

[57] ABSTRACT

A biopsy attachment 90 for a ultrasound probe 10 includes a frame 92 and a device 100, 102 for mounting the frame 92 to the probe 10 in order to align the frame 92 relative to the probe 10. The biopsy 90 attachment further includes a biopsy needle guide 106 and a device 94, 96 for pivotally moving the biopsy needle guide from an undeployed position, adjacent to an ultrasound transparent window 24, to a deployed position which is above and spaced from the ultrasound transparent window 24, in order to guide a biopsy needle 132 to the desired biopsy location.

15 Claims, 4 Drawing Sheets

FIG_1
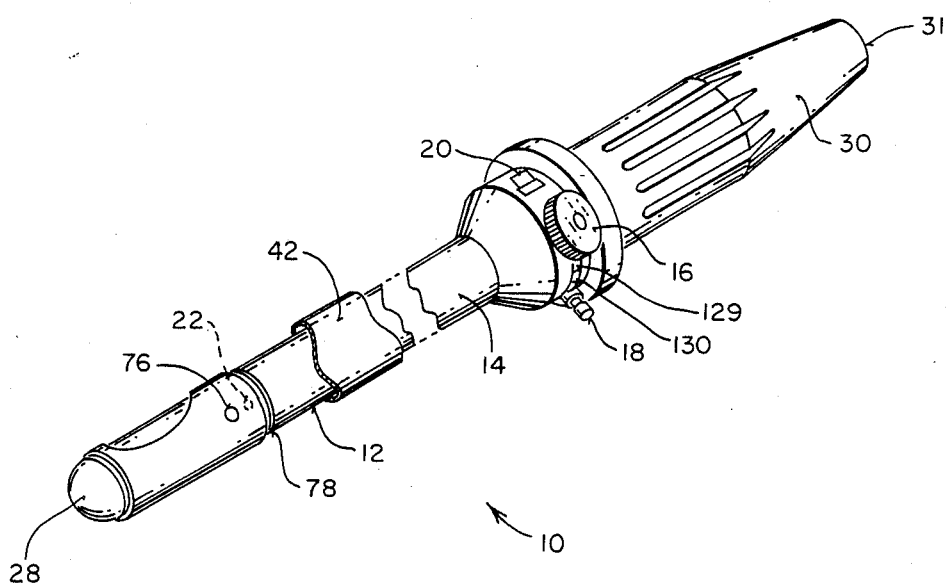
FIG_1A
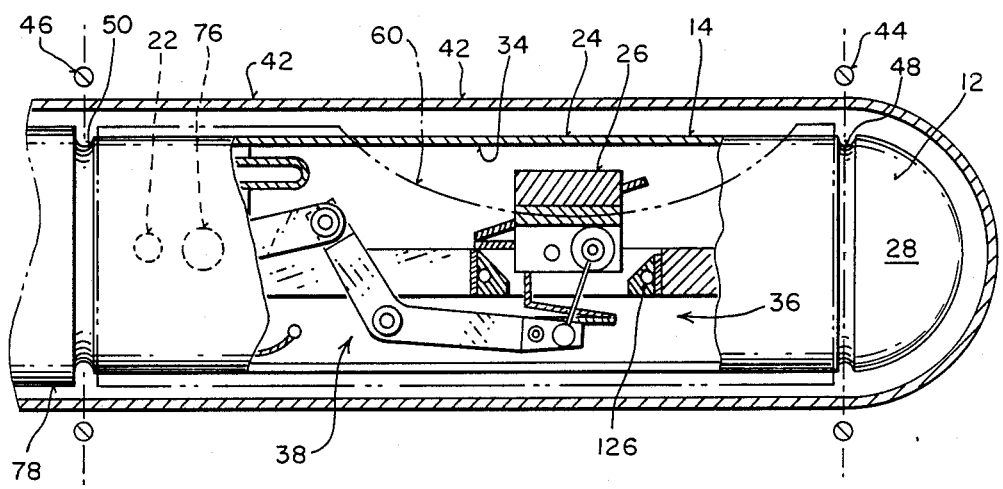

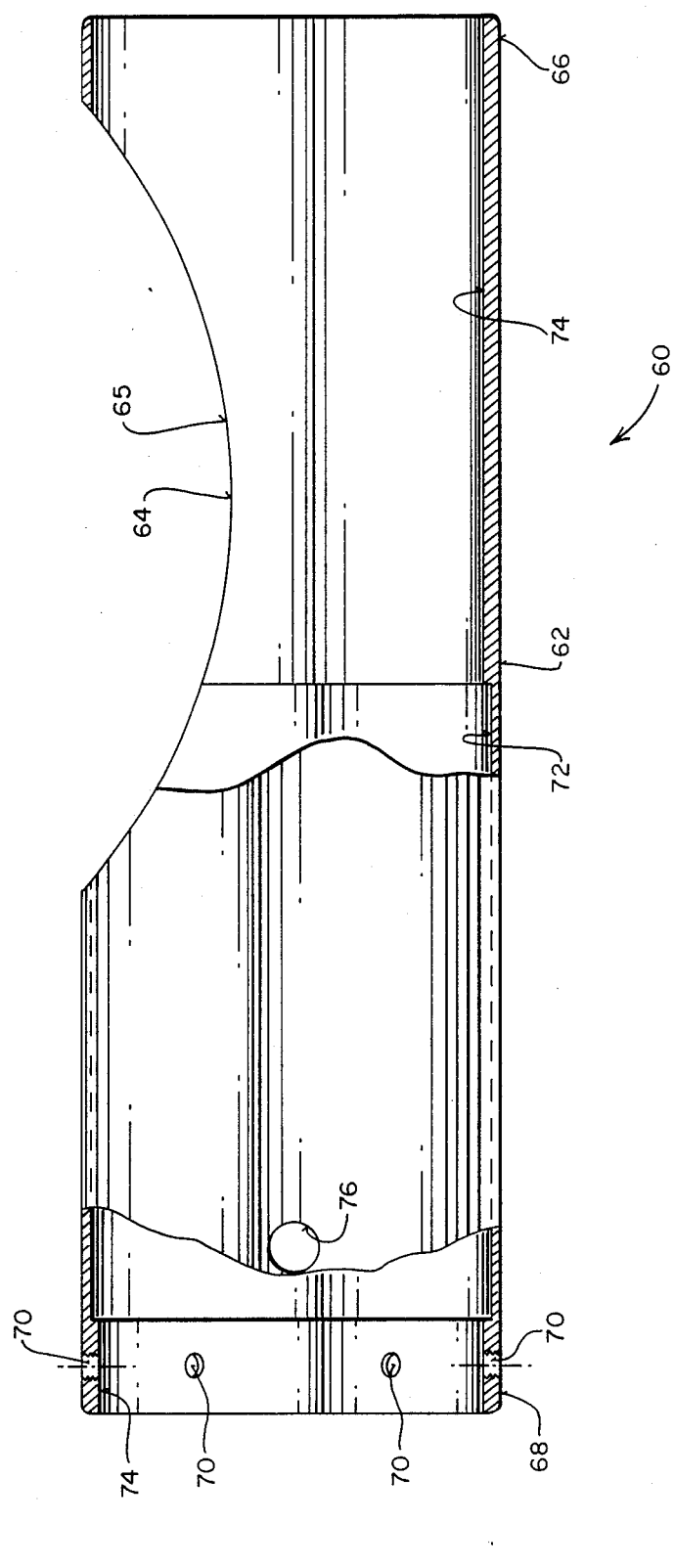
FIG_2

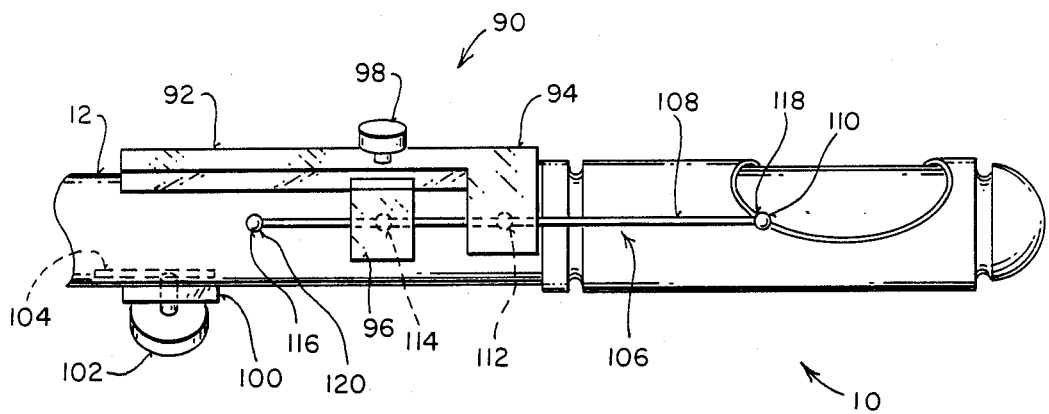
FIG_3
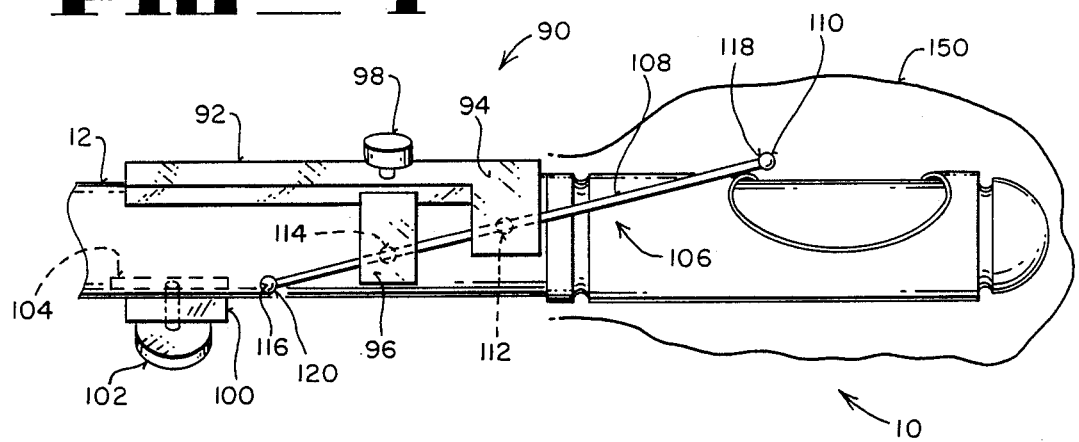
FIG_4
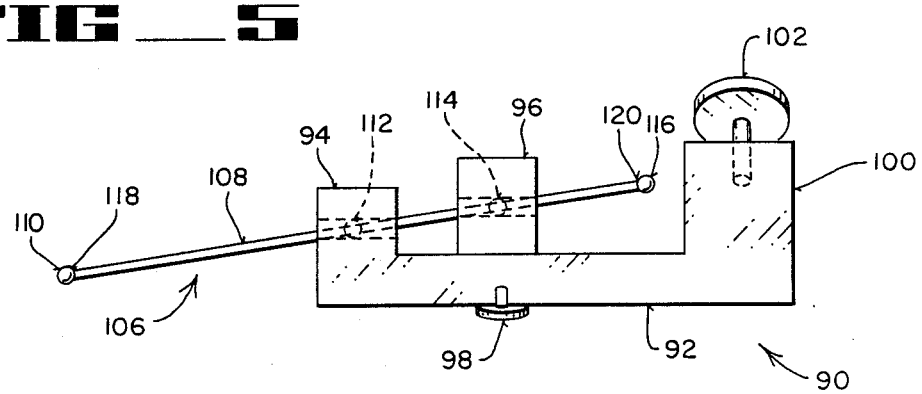
FIG_5

FIG_6
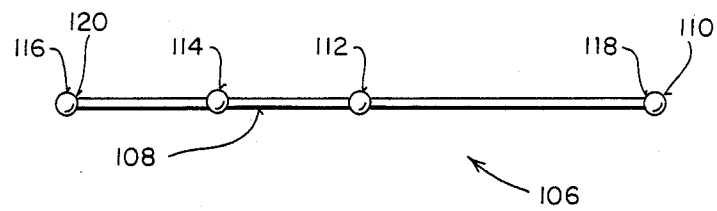
FIG_7
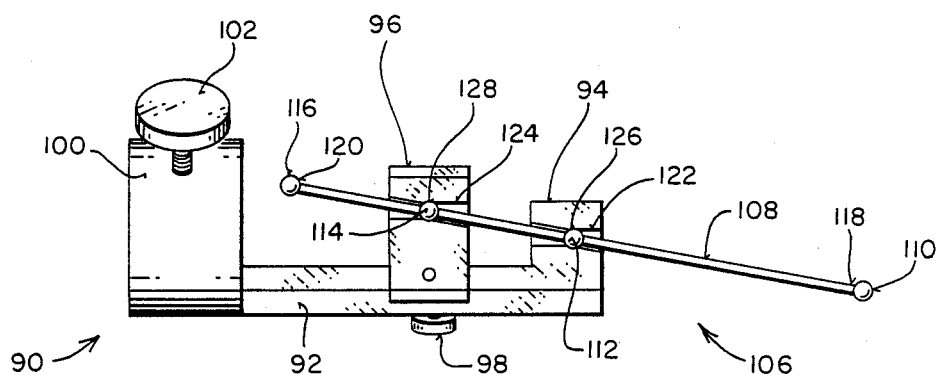
FIG_8
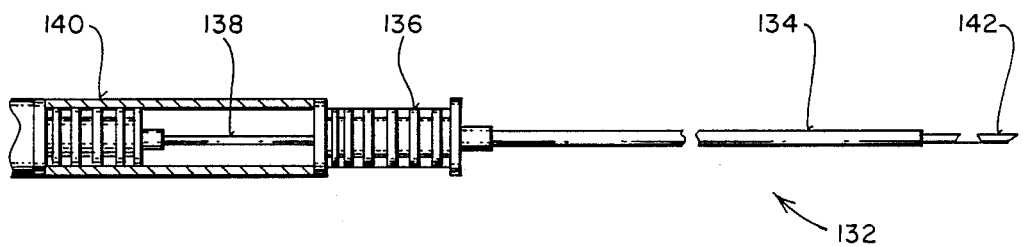

BIOPSY ATTACHMENT FOR ULTRASOUND PROBE

FIELD OF THE INVENTION

The present invention is directed to a biopsy attachment for a sensing probe, such as an ultrasound probe.

BACKGROUND ART

With certain sensing probes as for example ultrasound probes, it often desirable to be able to take a biopsy of suspect tissue identified by the sensing probe. It is desirable that this biopsy be taken during the procedure which employs the sensing probe in order to use the sensing probe to locate and maintain the position of the suspect tissue and to guide the biopsy device relative to the suspect tissue so that appropriate tissue can be collected.

There are a number of ultrasound probes currently available on the market. These include probes having a stationary linear array of ultrasound transducers, probes having an end fire wobble-type transducer and probes having a side fire wobble-type transducer. The latter side fire wobble-type transducer probe is disclosed in U.S. Pat. No. 4,756,311, granted July 12, 1988 and assigned to Diasonics, Inc., the present assignee hereof.

With all of these types of probes, it is possible to secure thereto a biopsy guide for a biopsy needle with essentially provides for a straight in biopsy. This is to say, the biopsy attachment guides the biopsy needle straight in and parallel to but spaced from the probe itself. While this type of biopsy arrangement is satisfactory, for a biopsy in the rectal area a procedure is required whereby a perineal puncture is made in order to take a biopsy of tissue adjacent the rectal area. It is more satisfactory and a simpler procedure to be able to place the biopsy device in through the sphincter muscle so that perineal tissue need not be punctured.

With respect to an end fire probe or a linear array probe, it is possible to provide a passage through the ultrasound probe which is disposed at an angle to the length of the probe itself. Through this passage, a biopsy needle can be positioned after the probe is disposed in the rectal area. Such an arrangement is not possible with a wobble-type side fire ultrasound probe due to the mechanisms such as the motor and linkage arrangements as well as the transducer mounts which take a considerable amount of space immediately adjacent the transducer and prevent the incorporation of a guide passage adjacent thereto.

One solution to this problem which was only recently developed includes a biopsy guide which can be secured externally to the ultrasound probe and include a curved guide passage for directing and bending a biopsy needle. This curved guide passage is inserted through the sphincter muscle. The curved guide passage then allows a biopsy needle to be inserted through the sphincter muscle and then deflected away from the ultrasound probe in order to be positioned for a biopsy. Such biopsy attachments have not proven to be totally satisfactory in that the biopsy needles are generally not rated for bending and there can be very substantial friction between the biopsy needle and the guide tube as the guide tube forces the biopsy needle to be bent.

SUMMARY OF THE INVENTION

The present invention is directed to improving upon the devices presently available.

The present invention includes a biopsy attachment for a sensing probe such as for example an ultrasound probe. The biopsy attachment includes a frame and means adapted for securing the frame to the ultrasound probe. The attachment further includes a biopsy needle guide. Means are provided for pivotally mounting the biopsy needle guide on the frame such that the biopsy needle guide can pivot from a first undeployed position to a second deployed position adapted for guiding a biopsy needle to a desired location.

The device for pivotally mounting the biopsy needle to the frame includes a first fixed leg and a second movable leg. A device is provided for pivotally mounting the biopsy needle guide relative to the first fixed leg and also relative to the second movable leg such that movement of the second leg causes the biopsy needle guide to pivot from the above mentioned first undeployed position which is adjacent to and runs parallel with the ultrasound probe to the second deployed position which is angled away from the ultrasound probe.

With such an arrangement, the biopsy needle guide can have an undeployed position which is substantially adjacent to and streamlined with the probe so that no extraordinary procedures need to be instituted in order to insert the ultrasound probe and biopsy needle guide into the cavity to be sensed. Further, once the probe and guide have been properly inserted, the guide itself can be conveniently pivoted to the appropriate deployed position so that a biopsy needle can be guided on a straight path through the biopsy needle guide in order to take appropriate biopsy.

Thus it is an object of the present invention to provide for a biopsy attachment for a probe and in particular an ultrasound probe.

It is a further object of the present invention to provide for a biopsy attachment which is easily and quickly securable to an ultrasound probe.

It is yet another object of the present invention to provide for a biopsy attachment which is streamlined with the probe upon insertion into a bodily cavity and which can allow a needle guide to be pivoted to a deployed position for the actual biopsy procedure.

It is yet another object of the present invention to provide for a biopsy attachment for use with a multiplane ultrasound probe such that the plane of the ultrasound probe can be adjusted to the coplanar with the plane of the biopsy needle guide in its deployed position, so that the biopsy procedure can be imaged with the ultrasound probe.

BRIEF DESCRIPTION OF THE DRAWINGS

FIG. 1 which is a perspective view of an embodiment of an ultrasound probe and a fluid jacket.

FIG. 1A is a cross-sectional view of FIG. 1.

FIG. 2 is a partial cross-sectional view of an embodiment of the fluid jacket of FIG. 1.

FIG. 3 shows an embodiment of the biopsy attachment of the invention positioned on the ultrasound probe as shown in FIG. 1 with the biopsy needle guide in an undeployed position.

FIG. 4 depicts the biopsy attachment of FIG. 1 placed in a bodily cavity with the biopsy needle guide deployed.

FIG. 5 depicts an embodiment of the biopsy attachment of FIG. 3 in substantially a front perspective view.

FIG. 6 depicts a biopsy needle guide of the invention.

FIG. 7 depicts a substantially back perspective view of the biopsy attachment depicted in FIG. 5.

FIG. 8 depicts a biopsy needle.

DETAILED DESCRIPTION OF THE PREFERRED EMBODIMENT

The present invention can be used with an ultrasound probe, such as the ultrasound probe found in U.S. Pat. No. 4,756,313, entitled "Ultrasonic Probe," granted July 12, 1988 and assigned to Diasonics, Inc. This U.S. Patent is incorporated herein by reference. Further a copending U.S. patent application, identified by Ser. No. 07/120,370, filed Nov. 13, 1987 and entitled, "External Fluid Jacket for Ultrasound Probe," and assigned to Diasonics, Inc. is incorporated herein.

As is seen in FIGS. 1 and 1A, an ultrasound probe 10 includes an elongated housing or body 12 which has a cylindrical side surface 14. The probe includes a thumbwheel 16 for rotationally positioning an ultrasound transducer sensor. The probe 10 further includes introduction and exit ports such as ports 18, 20 for introducing and removing fluid.

The probe 10 includes an internal water port 22 which is located adjacent to a window 24. The window 24 of probe 10 is formed as part of the elongated housing or body 12. An ultrasound transducer 26 for sending and receiving ultrasound signals is positioned in the probe immediately adjacent the window 24. The probe further includes a distal end 28 and a handle 30. A multipin connector (not shown) can be inserted into the end 31 of the handle 30 in order to connect the probe to the appropriate power supply and an appropriate computer device. The computer device provides an electrical signal to the ultrasound transducer 26 and receives from the ultrasound transducer 26 an appropriate response, and from the probe 10 a position signal. With the signal from the transducer 26 and the position signal, the computer device can create an ultrasound image of the tissue being sensed.

The ultrasound transducer 26 which is located adjacent the window 24 is contained in a fluid filled chamber 34. The chamber allows the transducer 26 sufficient space to enable it to move in all the desired directions and additionally to house the mounts 36 which mount the transducer 26 and also the linkage arrangement 38 which cause the ultrasound transducer 26 to move as desired.

The internal fluid port 22 is as close as possible to the chamber 34 and the window 24 in order to provide, as indicated above, the fluid adjacent to the transducer 26 to fill a sheath 42 with fluid. Properly filled, the sheath 42 can fill an internal body cavity, providing a continuum for the ultrasound signal. The sheath 42 in a preferred embodiment is made out of a latex rubber. The sheath is held in position by bands 44 and 46 which cause the sheath 42 to be urged into grooves 48 and 50 provided in the probe 10.

An embodiment of the invention includes a fluid jacket 60 which includes a tubular, cylindrical body 62 which is disposed about the window 24 and the cylindrical side surface 14 of the probe 10. In a preferred embodiment, the fluid jacket 60 is comprised of stainless steel. However, other materials can be used and be within the scope of the invention.

The cylindrical body 62 of the fluid jacket 60 includes an opening 64 which in a preferred embodiment is substantially elliptical. Other opening configurations can be used as long as the opening accomodates the full range of movements of the transducer 26. In other words, the opening must be large enough so that the ultrasound signal sent from or received by the transducer is not blocked or in any way impaired by the fluid jacket 60.

The fluid jacket 60 includes first and second ends 66 and 68. The internal diameter of each of these ends is slightly larger than the external diameter of the cylindrical side surface 14 of the probe 10. Thus, the fluid jacket 60 can be slid over the cylindrical side surface 14 into a place on the probe 10. A plurality of set screws 70 are disposed adjacent to the second end 68 in order to secure the fluid jacket 60 to the housing 12 of the probe 10.

As can be seen in FIG. 2, the fluid jacket 60 includes a recessed portion 72 which has an internal diameter which is slightly larger than the internal diameter of the fluid jacket 66 as located at the first and second ends 66, 68. This recessed portion 72 is positioned so that it is located adjacent to and above the internal probe port 22. Further the recessed portion extends to at least part of the opening 64. As can be seen in FIG. 2, the recessed portion 72 is cylindrical and extends completely around the internal cylindrical surface 74 of the fluid jacket 60. It is to be understood that the recessed portion 72 can extend so that it contacts more of the edge 65 of the opening 64. As shown in FIG. 2, about a quarter of the edge 65 of the opening 64 is directly communicated with the recessed portion 72. Thus fluid exiting from probe port 22 can communicate through the recessed portion 72 directly with that portion of the edge 65 which communicates with the recessed portion 72.

Fluid jacket 60 includes a port 76 which is provided through cylindrical body 62 at a location which is adjacent to but offset from the internal port 22 of the probe 10 so that the internal port 22 and the fluid jacket port 76 are not aligned. Further the port 76 of the fluid jacket 60 is provided at a location which communicates with the recess portion 72.

A retainer band 78 is provided in a position which is spaced from the second groove 50 in order to facilitate proper positioning of the band 46 which retains sheath 42.

As can be seen in FIG. 3, the biopsy attachment 90 of the invention includes a frame 92 which has a first fixed leg 94 and a second movable leg 96. Using thumbscrew 98 movable leg 96 can be moved from a first undeployed position as shown in FIG. 3 to a second deployed position as shown in FIG. 4.

The biopsy attachment 90 includes a third curved arm 100 which wraps around the ultrasound probe 10 in order to hold the frame 92 in position relative to the probe 10. Disposed through the third curved arm 100 is a thumbscrew 102 which can be received by an alignment groove 104 formed in the body 12 of the probe 10. With the thumbscrew 102 received in the alignment groove 104, the frame 92 and thus the biopsy attachment 90 is properly aligned with respect to the probe 10.

The biopsy attachment 90 includes a disposable biopsy needle guide 106 which is comprised of a tube 108 which can be comprised of stainless steel as can all of the above mentioned portions of the biopsy attachment 90. Further the biopsy needle guide 106 includes four spherical members 110, 112, 114, and 116, which are deployed along the length of tube 108 with spherical members 110 and 116 positioned at the front biopsy end 118 of the needle guide 106 and the spherical member 116 positioned at the back insertion end 120 of the biopsy needle guide 106. These spherical members can be comprised of Delrin ® or other comparable materials. The needle guide 106 is disposable and is replaced after each biopsy procedure.

The spherical members 112 and 114 are received in butterfly-shaped grooves 122 and 124 of first fixed leg 94 and second movable leg 96 respectively. First and second butterfly-shaped grooves 122 and 124 include a central cylindrical bore 126 and 128 respectively which receive the spherical members 112 and 114 in a retaining way so that the biopsy needle guide 106 when inserted in the first and second butterfly-shaped grooves 122 and 124, with the frame 92 properly secured to the probe 10, will retain the biopsy needle guide 106 relative to the frame 92. The butterfly-shaped grooves 122 and 124 allow the needle guide 106 to pivot back and forth as the second movable leg 96 is moved relative to the frame 92. It is to be understood that in alternate embodiments, only one of the spherical members 112 or 114 need be used in order to properly secure the biopsy needle guide 106 relative to the frame 92 and to accomplish the positioning of the biopsy needle guide 106 from an undeployed to a deployed position in order to obtain a biopsy.

As can be seen in FIG. 3, in an undeployed position, the spherical member 110 of the biopsy needle guide 106 is positioned immediately adjacent the window 24 for the transducer 26. In such a position, at least a portion of the spherical member 110 is below the outer surface of the fluid jacket 60. Thus the spherical member 110 and the biopsy needle guide 106 present a streamlined appearance when they are inserted into a cavity with the probe for purposes of the medical procedure.

The spherical member 116 assists in locating end 120 of the needle guide 106 so that biopsy needle 132 can be easily placed into tube 108.

As previously indicated, the probe 10 itself includes a thumbwheel 16 for rotating the transducer by the use of wire 126. As probe 10 is a wobbler-type probe, the pivoting back and forth of the ultrasound transducer 26 defines a plane. With the use of thumbwheel 16, this plane can be rotated such that multiple planes can be addressed with the probe. The thumbwheel 16 further includes a detent 129 which can be received in a groove 130 for positioning the transducer 26 in a plane which is coplanar with the biopsy needle guide 106 as deployed in FIG. 5. With this arrangement, the transducer can sense the position of the biopsy needle guide 106 and of the biopsy probe 132 (FIG. 8) as it is positioned through the biopsy needle guide 106.

As can be seen in FIG. 8, the biopsy needle assembly 132 includes a cannula 134 having a handle 136 and a biopsy needle 138 disposed through the cannula 134. The biopsy needle 138 includes a handle 140 and a biopsy end 142.

INDUSTRIAL APPLICABILITY

The operation of the biopsy attachment 90 is as follows.

With the biopsy needle guide 106 of the biopsy attachment 90 in an undeployed position as shown in FIG. 3, the biopsy attachment 90 and the probe 10 are inserted into a cavity such as rectal cavity 150 in FIG. 4 through a muscle such as sphincter muscle 152 so that the transducer 26, which is located below the window 24 can be appropriately positioned to image the desired tissue. It is to be understood that except for the front biopsy end 118 and the portion of the tube 108 adjacent thereto no other part of the biopsy attachment 90 is inserted through the sphincter muscle 152 in order to present the most streamlined presentation possible. Thus the biopsy attachment 90 is not urged through the sphincter muscle 152. With the probe 10 and the biopsy attachment 90 so positioned relative to the sphincter muscle 152 and the cavity 150, using the movable leg 96, the biopsy needle guide 106 can be deployed to a position spaced away from and above the window of the probe 10. In such a position, the biopsy needle guide 106 is properly oriented in order to position the biopsy needle 132. The biopsy needle assembly 132 can then be used to obtain a biopsy and then removed from the biopsy attachment 90. The biopsy needle guide 106 is then moved to the undeployed position as shown in FIG. 3 by repositioning movable leg 96 so that the probe can be removed from the cavity.

Thus it can be seen that the present invention provides for a biopsy attachment 90 which improves upon available biopsy attachments by presenting a streamlined presentation for insertion to the bodily cavity without requiring that the biopsy needle itself be bent in order to be properly positioned relative to the desired tissue and without requiring a perineal puncture.

Other objects and advantages of the invention can be obtained from a review of the figures and the appended claims.

It is to be understood that other embodiments of the present invention can be provided and fall within the breadth and scope of the appended claims.

I claim:

1. A biopsy attachment for an ultrasound probe, wherein said probe includes an insertable section for inserting into a cavity of a subject, comprising:
   a frame;
   means for securing said frame externally to the ultrasound probe at an adjacent location on said insertable section;
   a biopsy needle guide;
   means for mounting said biopsy needle guide on said frame such that the biopsy needle guide pivots from a first undeployed position, wherein said insertable section and said biopsy needle guide, located on said insertable section can be efficiently positioned in the cavity, to a second deployed position adapted for guiding a biopsy needle, such that in the second deployed position a portion of said biopsy needle guide is pivoted to a position away from the insertable section and proximal to the scan window of said ultrasound probe.

2. The apparatus of claim 1, wherein said mounting means includes:
   a fixed leg extending from said frame;
   a movable leg;
   means for movably securing said movable leg to said frame so that there can be movement of said movable leg relative to said frame;
   means for pivotally mounting said biopsy needle guide on said fixed leg;
   means for pivotally mounting said biopsy needle guide on said movable leg, such that the movement of said movable leg causes said biopsy needle guide to pivot from said undeployed position to said deployed position adapted for guiding a biopsy needle to a location predetermined with said ultrasound probe.

3. The apparatus of claim 2, wherein the ultrasound probe includes a biopsy attachment alignment groove, said means adapted for securing said frame to the ultrasound probe including means adapted for engaging the alignment groove.

4. The apparatus of claim 3, including means for lockingly positioning said second movable leg in a first position with the needle guide undeployed and a second position with the needle guide deployed.

5. The apparatus of claim 4, wherein said means for pivotally mounting said biopsy needle guide in said fixed and said movable leg includes a butterfly shaped groove which allows said biopsy needle guide to pivot in at least one plane.

6. The apparatus of claim 5, wherein said biopsy needle guide includes an elongated tube and a spherical member located along said elongated tube; and
wherein said butterfly shaped groove includes means for retaining said spherical member in one position while allowing said biopsy needle guide to pivot.

7. The apparatus of claim 6, wherein said ultrasound probe including a ultrasound scan window with a fluid delivery jacket spaced above said window, said apparatus further comprising:
said biopsy needle guide including a biopsy collection end, adapted to be partially received in the space between the fluid delivery jacket and said ultrasound scan window in order that said fluid delivery jacket at least partially covers the biopsy collection end, streamlining the combination of said biopsy needle guide, externally mounted on said insertable section of said probe such that insertion into the cavity of the subject is smoothly promoted.

8. The apparatus of claim 7, with the ultrasound probe including an ultrasound transparent window with a fluid delivery jacket spaced above and surrounding the window, the jacket having a front end and a back end located on opposite sides of the window, the probe intended for insertion into the cavity of a subject such that the jacket and window are located inside the cavity with any tissue which defines the entrance of the cavity disposed about only the back end of the fluid jacket and wherein the apparatus further comprises:
said means, adapted for securing said frame to the probe, allows said frame to be secured adjacent to the entrance defining tissue and outside of the cavity with the biopsy needle guide located at least partially inside the cavity and adapted to be adjacent said window such that said frame is not inserted into the cavity.

9. A biopsy attachment adapted for mounting a biopsy needle guide relative to an ultrasound probe, which probe includes an insertable section at one end for insertion into a cavity of a subject, comprising:
a frame;
means adapted for securing said frame externally adjacent to the ultrasound probe on said insertable section;
means adapted for mounting said biopsy needle guide on said frame, wherein said mounting means comprises:
a first leg fixedly mounted and extending from said frame;
a second leg;
means for movably securing said second leg to said frame such that said second leg moves relative to said frame;
means for mounting said biopsy needle guide on said first leg;
means for mounting said biopsy needle guide on said second leg; wherein the movement of said second leg causes said biopsy needle guide to move from an undeployed first position to a deployed second position, such that said movement causes said biopsy needle guide to pivot in at least one plane.

10. A removable biopsy needle guide adapted for use with a biopsy attachment of an ultrasound probe, having an insertable section for inserting into a cavity of a subject, wherein said biopsy attachment is comprised of a frame;
means for securing the frame to the external surface of said ultrasound probe at a location on said insertable section;
said frame including a fixed first leg and a movable second leg;
means for movably securing said movable second leg to the frame such that movement of said movable second leg is relative to said frame;
means for pivotally mounting said biopsy needle guide on said fixed first leg;
means for pivotally mounting said biopsy needle guide on said movable second leg, such that the movement of said movable second leg causes said biopsy needle guide to pivot from a first undeployed position, wherein said biopsy needle guide is adapted to be at a location adjacent to the insertable section so that the biopsy needle guide and the insertable portion can be smoothly positioned in the cavity, to a second deployed position adapted for guiding a biopsy needle to a predetermined location, wherein in the second deployed position at least a portion of said biopsy needle guide is pivoted to a position away from the insertable section;
said removable biopsy needle guide comprising:
an elongated tube;
first retaining means located along said elongated tube adapted for being received in and retained by one of the mounting means of said fixed first leg and said movable second leg so that as said biopsy needle guide is pivoted by the biopsy attachment, said biopsy needle guide is not dislodged from said biopsy attachment.

11. The biopsy needle guide of claim 10 wherein:
said first retaining means includes a spherical member adapted to be received in a retaining recess defined by the mounting means of one of the first fixed and second movable legs.

12. The biopsy needle guide of claim 11, wherein:
said elongated tube has first and second ends; and
said biopsy needle guide including second and third spherical members located on said first and second ends respectively.

13. A multiplane ultrasound probe, which probe includes an insertable section provided for insertion into a cavity of a subject, with a biopsy attachment comprising:
said multiplane ultrasound probe including:
a probe body including a biopsy attachment alignment groove;
an ultrasound transducer located in said insertable section;

an internal cavity defined in said body for housing said transducer;

means for pivotally and rotationally mounting said transducer so that said transducer can pivot back and forth in any number of planes selected by rotating said transducer;

said biopsy attachment including:

a frame;

means for securing said frame to the ultrasound probe, at a location next to the insertable section, such that the frame is aligned with the alignment groove;

a biopsy needle guide;

means for pivotally mounting said biopsy needle guide to said frame so that said biopsy needle guide can be caused to pivot from a first undeployed position, wherein said biopsy needle guide is adapted to be at a location next to the insertable section so that the biopsy needle guide and the insertable portion can be efficiently urged into the cavity, to a second deployed position, wherein in the second deployed position at least a portion of said biopsy needle guide is pivoted to a position away from the insertable section in order to address the desired location in order to take a biopsy; and said transducer rotatable to a plane which contains said biopsy needle guide in a deployed position in order to monitor the biopsy needle guide.

14. The apparatus of claim 13 wherein said probe includes:

detent means for causing said pivotally and rotationally mounting means to stop rotating said transducer in a plane which includes said biopsy needle guide in a deployed position.

15. The apparatus of claim 14 wherein said biopsy needle guide pivotally mounting means includes:

a first fixed leg extending from said frame;

a second movable leg;

means for movably securing said second movable leg to said frame so that there can be movement of said second movable leg relative to said frame;

means for pivotally mounting said biopsy needle guide on said first fixed leg;

means for pivotally mounting said biopsy needle guide on said second movable leg, such that the movement of said second movable leg causes said biopsy needle guide to pivot from a first undeployed position to a second deployed position adapted for guiding a biopsy needle to a desired location.

* * * * *